United States Patent [19]

Uschold et al.

[11] Patent Number: 5,531,758
[45] Date of Patent: Jul. 2, 1996

[54] SLIDING REDUCER SEAL FOR SURGICAL TROCAR

[75] Inventors: Robert C. Uschold, Cincinnati; Randy R. Stephens, Fairfield, both of Ohio; Jeffrey Mauch, Lynchburg, Va.; Richard C. Smith, Loveland; Kevin Houser, Centerville, both of Ohio

[73] Assignee: Ethicon Endo-Surgery, Inc., Cincinnati, Ohio

[21] Appl. No.: 217,991

[22] Filed: Mar. 25, 1994

[51] Int. Cl.$^6$ .................................................. A61M 5/00
[52] U.S. Cl. ........................... 606/185; 604/167; 604/264
[58] Field of Search ................................... 606/184, 185; 604/164, 165, 167, 160, 161, 168, 169, 158, 159, 178, 264, 272, 51

[56] References Cited

U.S. PATENT DOCUMENTS

| 5,104,383 | 4/1992 | Shichman | 604/167 |
| 5,112,321 | 5/1992 | Hiltebrandt | 604/264 |
| 5,221,264 | 6/1993 | Wilk et al. | 604/167 |
| 5,397,335 | 3/1995 | Gresl et al. | 606/185 |

*Primary Examiner*—Michael H. Thaler
*Assistant Examiner*—William Lewis
*Attorney, Agent, or Firm*—Paul A. Coletti

[57] ABSTRACT

A reducer seal which fits within the cannula handle of the trocar. Contained on the reducer seal there is a seal retainer. Contained on the seal retainer there is a track and movable on the track there is a slide. The reducer track is attached to the trocar housing. The reducer seal retainer is attached to the slide and holds the reducer seal in place. The reducer slide then snaps onto the reducer track. In an "open" position the reducer slide is held away from an opening in the reducer. Detents on the reducer track hold the reducer in this position. Transverse motion moves the reducer into an active or "closed" position. The reducer seal slides into frictional engagement on the sealing surface of the reducer track. The reducer has a smaller diameter opening than the trocar cannula.

14 Claims, 5 Drawing Sheets

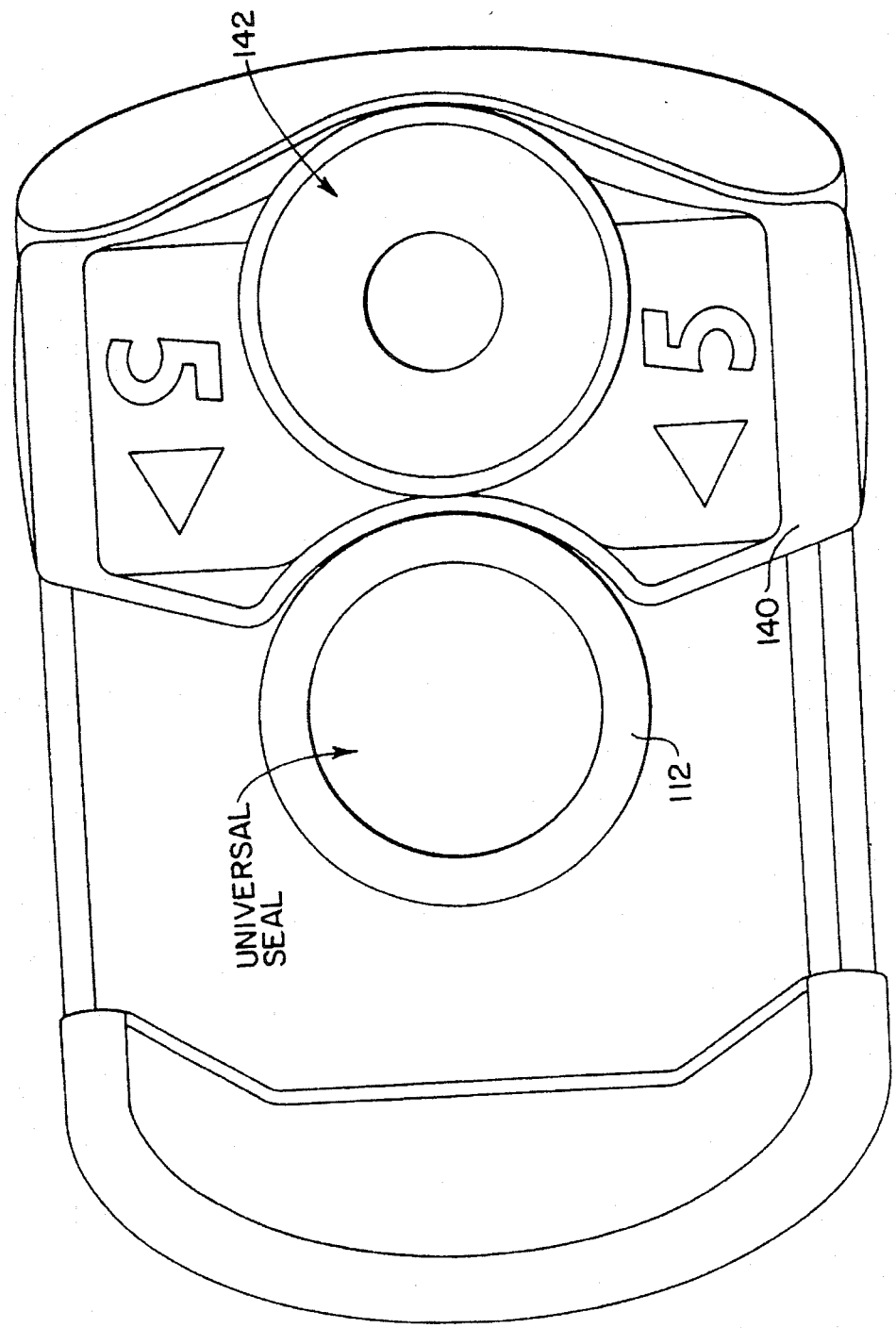

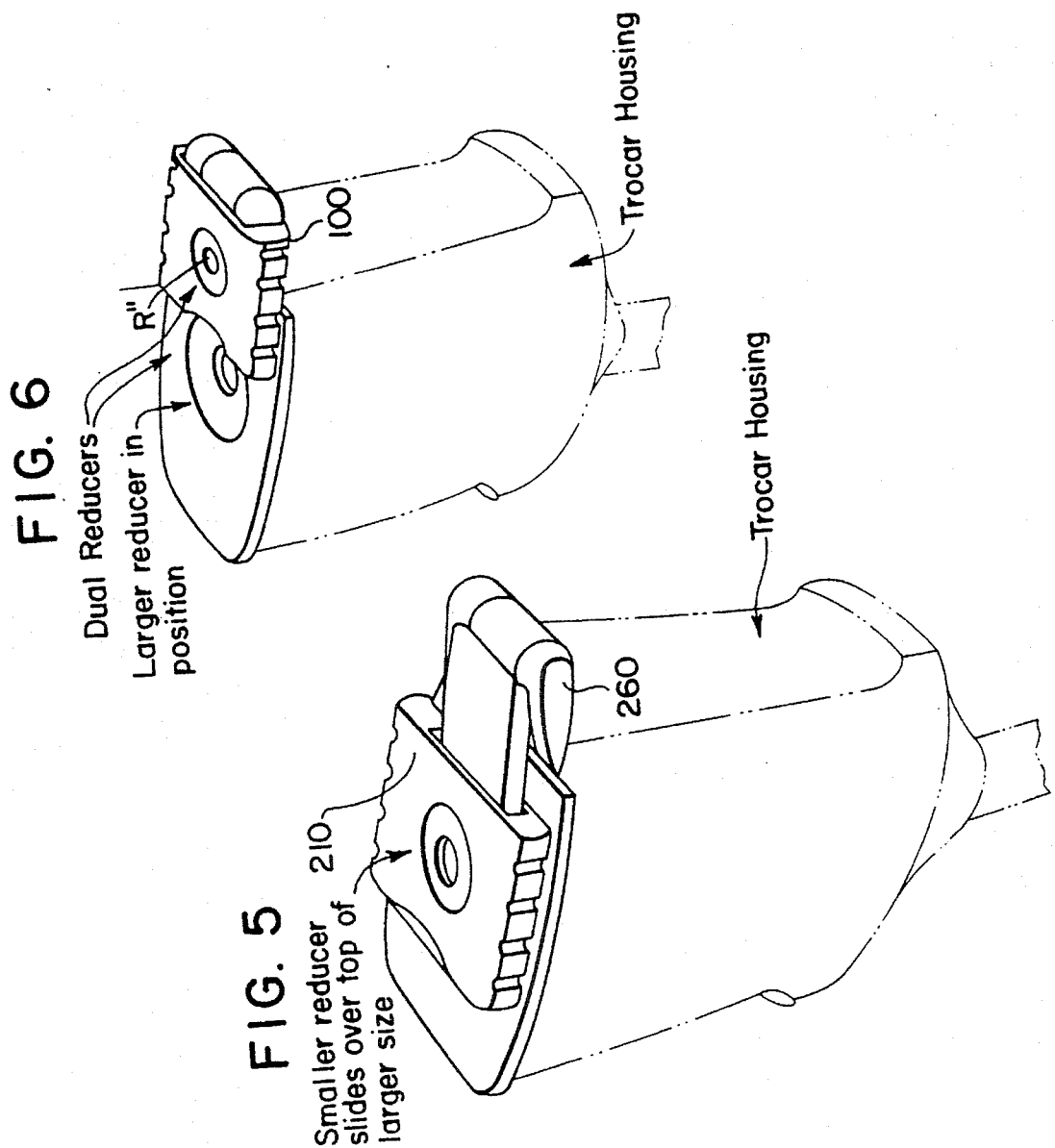

SLIDING REDUCER SEAL FOR SURGICAL TROCAR

FIELD OF THE INVENTION

This invention relates generally to surgical trocar cannulas, and more particularly to cannulas which provide fluid tight seals around laparoscopic instruments of various diameters.

BACKGROUND OF THE INVENTION

In medical procedures such as laparoscopy, the patient's abdomen is distended to allow access to and visibility of the abdominal cavity. In order to distend the abdominal cavity, carbon dioxide gas is injected within the cavity. Gas insufflates the abdominal cavity, supporting the abdominal walls up and away from the internal organs. Without this pressure, the abdominal wall collapses and the visibility through a laparoscopic camera is lost.

While the abdomen is filled with gas, a trocar cannula (through which medical instruments can be inserted) transverses the abdominal wall. Valves are typically included in these cannulas to prevent gas from leaking from the pressurized cavity when the laparoscopic cannula is in use. Competence of these valves is desirable, in that even a small leak in the valve may cause a decrease in insufflation pressure and possibility of desufflation of the abdomen.

A variety of instruments are used with such cannulas. For example, forceps, clamps, scalpels, graspers, clip appliers, staplers, and dissectors are all known. These instruments typically have round cross sections and have outer diameters ranging from about 1 mm to about 30 mm. In many laparoscopic procedures it is necessary to remove a large diameter laparoscopic instrument and to replace it with a small laparoscopic instrument during the course of the procedure. In this event, it is not practical to replace the cannula at such times.

On the other hand, laparoscopic cannulas are available with lumen diameters of 5 mm, 7 mm, 10 mm, 12 mm, 18 mm, and 33 mm or other known sizes, with the larger sizes being preferred for laparoscopic procedures in which larger diameter laparoscopic instruments may be required. The valves used in such cannulas may be any valve which seals around medical instruments, such as those valves described in U.S. Ser. No. 899,397, filed Jun. 16, 1992, and incorporated herein by reference. However, all single valve systems may leak when small laparoscopic instruments are used in relatively large diameter trocar cannulas. A need has therefore existed for a universal cannula which may be adapted rapidly to accept instruments of varying sizes, and to provide a fluid tight seal around such instruments.

Some solutions have been offered. For instance, Stouder Jr., U.S. Pat. No. 5,211,633 discloses a surgical cannula with selectable seals which assure a fluid-tight fit around medical devices of a variety of sizes. The cannula includes a tubular member insertable into a patient and having a side wall defining a lumen through which a medical device may be inserted. The cannula also includes a housing mounted to a proximal end of the tubular member wherein the housing has a passage allowing insertion of a medical device therethrough and into the lumen. A movable member is mounted to the housing and is selectively movable between a first position and a second position across the passage. When the movable member is in its first position the passage accommodates insertion of a first medical device having a first outer cross-sectional dimension. A first valve body is mounted in the movable member and has a first opening therein corresponding in size to the outer cross-sectional dimension of a smaller second medical device, wherein the first opening is smaller than the passage. When the movable member is in its second position the first valve body provides a fluid tight seal around the second medical device.

In Ritchart et al., U.S. Pat. No. 5,209,737, a septum valve in a trocar assembly has a variable orifice that is responsive to a cross-sectional dimension of the surgical instrument being inserted into the trocar channel, thereby minimizing leakage of inflation gas from the body cavity, such as the abdomen, being operated on. An elastomeric septum is disposed in the channel and includes portions which define an orifice having in a relaxed state a first cross-sectional area. An actuation assembly provided with levers which pivot radially outwardly to expand the seal and thereby expand the orifice to the second cross-sectional area in response to entry of the instrument into the channel. The actuation assembly is free to float in an annular recess to accommodate an instrument which is misaligned with the trocar channel.

In Powers, U.S. Pat. No. 5,211,370, a variable orifice sealing valve is made from a thin, elastic cylinder. The cylinder is retained at both ends, and one end is twisted with respect to the other end thereby reducing the fluid flow path through the center of the cylinder. The device is particularly useful for medical procedures such as in conjunction with a catheter.

U.S. Pat. No. 5,197,955, incorporated herein by reference discloses a trocar assembly device that includes an improved seal assembly that accommodates instruments having a wide range of diameters. The seal assembly includes a universal seal member that is generally of hourglass shape defining converging and diverging side walls that form a constricted center bore portion therebetween. Various alternative means are provided to either increase or decrease the inner diameter of the center bore portion of the seal member.

Ser. No. 046,587, filed Apr. 12, 1993 (END-3) Stephens et al., incorporated herein by reference discloses an improved elastomeric seal member to maintain sealing engagement during off-centering or radial motion of instruments extending therethrough. The seal members include an inner section and an outer section. The inner section has an opening formed therein to permit an elongate instrument to pass therethrough in sealing engagement therewith. In accordance with certain embodiments, a corrugated portion is formed in the outer section. In accordance with certain embodiments an annular floating ring separates the inner section from the outer section.

Ser. No. 028,453, filed Mar. 9, 1993 and also incorporated herein by reference discloses an adaptor cap assembly is provided for a trocar, consisting of a base which contains an opening which is the same size as the opening of the trocar cannula handle. There is also a cap integrally attached to the base which contains a gasketing assembly wherein the assembly is of a smaller diameter than the diameter of the trocar cannula handle opening in the base of the adaptor cap assembly. This cap is hingedly attached to the base so that it can be flipped by using the thumb either into or out of alignment with the openings of the trocar cannula handle and the base of the adaptor cap assembly. Thus, this mechanism can be used so that a smaller diameter instrument can be placed within a larger diameter opening (with the adaptor cap in place), or, the adaptor cap can be moved out of place so that a larger diameter mechanism can be inserted within the adaptor cap assembly and into the trocar cannula handle, with both the base and the trocar cannula handle having the same size opening.

U.S. Pat. No. 5,104,383 to Schichman describes a valve wherein an adapter seal for use with a cannula assembly is provided. The adapter seal is provided with a stabilizer plate to limit the movement of an instrument relative to the seal.

SUMMARY OF THE INVENTION

Yet, for all capabilities of the devices disclosed in the previously cited patents, there are certain disadvantages attendant to such solutions. In particular, none of the mechanisms described above combine the following four criteria:
A) the capability of being maintained on the trocar while in use;
B) adding a low overall length dimension to the cannula handle of the trocar. This is important in that the less height added, the less of concern there is of the length of the laparoscopic instrument being used;
C) ease of moving in and out of position, that is, convenience to the surgeon while operating between one instrument and another;
D) ease of removal, when desired, so that the surgeon is capable of readily exchanging reducer mechanisms or, in fact, using larger diameter instruments if desired.

The present invention consists of four pieces which form a mechanism to address these concerns. There is disclosed herein a reducer seal which fits within the cannula handle of the trocar. Contained on the reducer seal there is a seal retainer. Contained on the seal retainer there is a track and movable on the track there is a slide. The reducer track is attached to the trocar housing. The reducer seal retainer is attached to the slide and holds the reducer seal in place. The reducer slide then snaps onto the reducer track. In an "open" position the reducer slide is held away from an opening in the reducer. Three detents on the reducer track hold the reducer in this position. Transverse motion moves the reducer into the active or "closed" position. The reducer seal slides into frictional engagement on the sealing surface of the reducer track. A latch on the reducer slide extends beyond the end of the reducer track and holds the reducer in place, unless the latch itself is lifted. Thus, the device is capable of being held in place when desired and is also quite easy to move when desired.

DESCRIPTION OF THE DRAWINGS

The present application will be better understood in conjunction with the drawings provided, in which:

FIG. 4 is a top view of the seal in place in the "open" position; and

FIGS. 5, 6 and 7 are perspective views of an alternate embodiment of the present invention.

DESCRIPTION OF THE INVENTION

Figure 1:
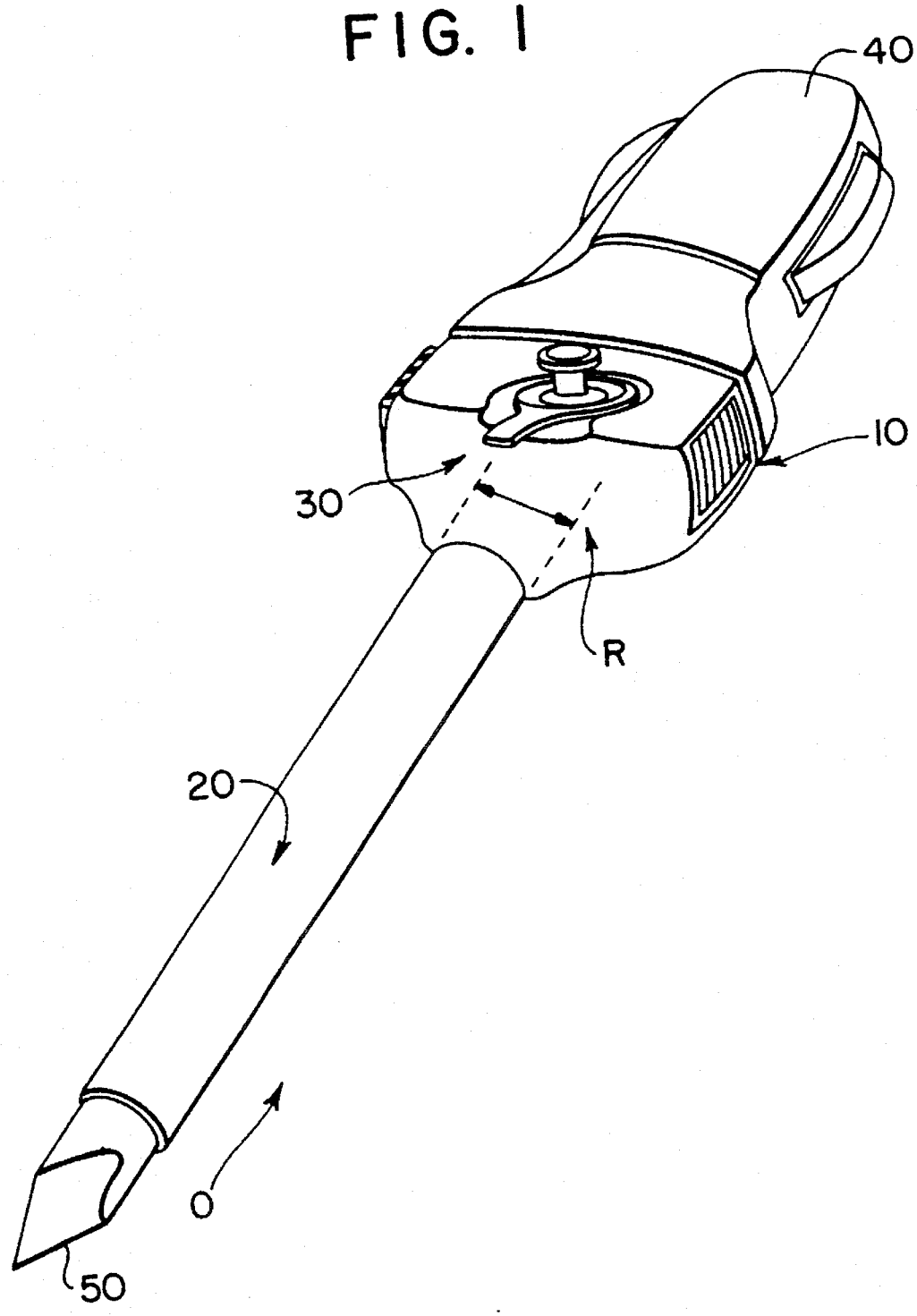
FIG. 1 is a perspective view of trocar showing an obturator handle and a cannula handle.

As seen in the present invention described in FIGS. 1–4 there is described herein a reducer sealing device 100 which fits within a surgical trocar 10. The trocar 10 itself generally has a cannula 20 which is a hollow tube attached to a cannula handle 30. The cannula handle 30 is matable with a obturator handle 40. The obturator handle 40 is attached to an obturator 50 which is insertable into the cannula. The obturator is generally a sharp instrument which is capable of piercing body tissue.

As seen in the perspective view of FIG. 1 the cannula handle 30, and consequently the cannula 20 have an opening of a certain inner diameter dimension R. In conjunction with this invention this dimension is anywhere from 5 mm to 33 mm. The present invention is capable of being inserted into a lip 32 created in the cannula handle, and therefore may be provided integrally with the cannula handle 30 before sale. Alternatively, the present invention may be inserted in this lip 32 after purchase of the cannula handle 30, and sold as a separate instrument. Of course, either function is an option which will not depart from the spirit of the invention.

Figure 2:
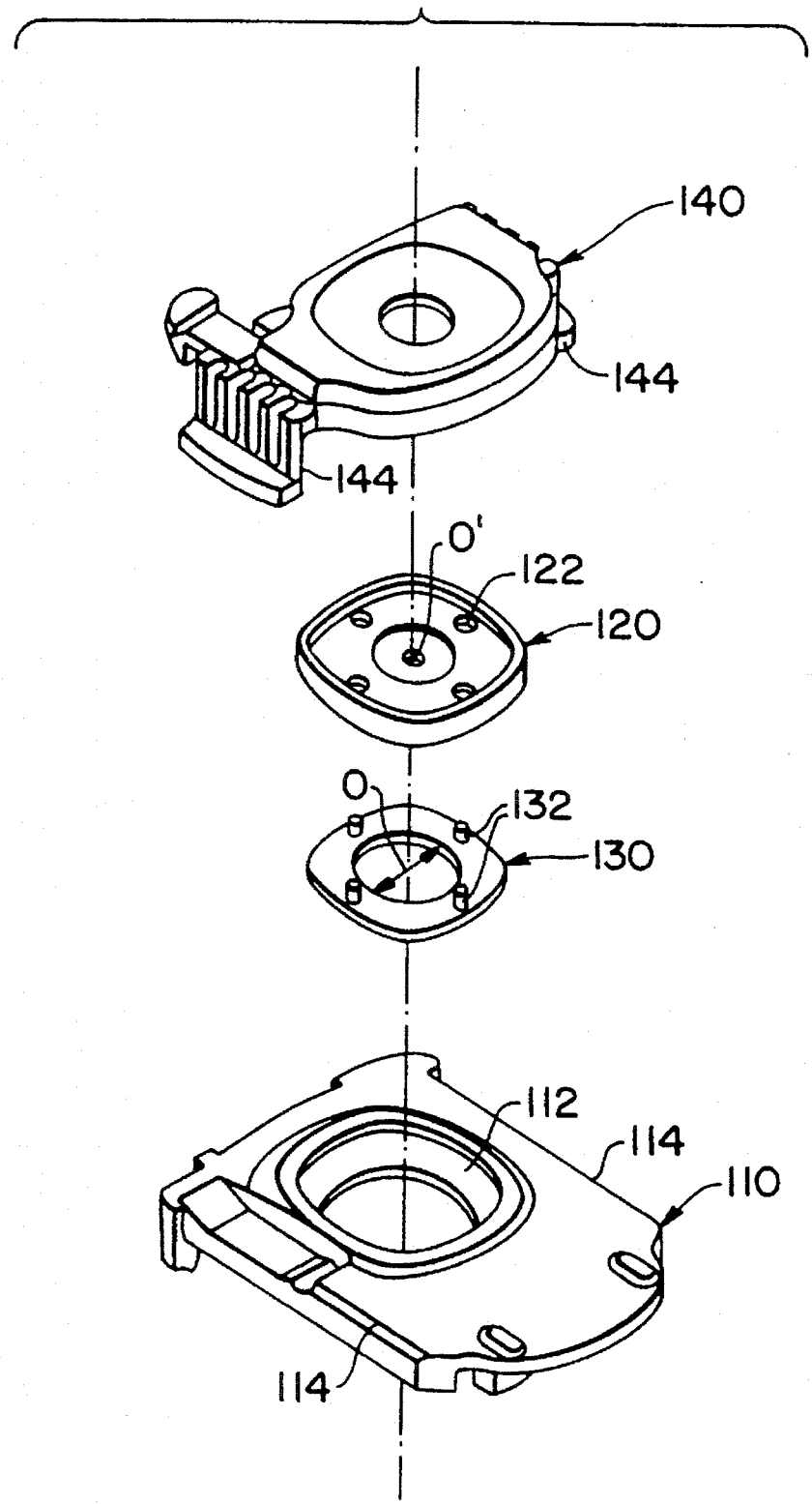
FIG. 2 is an assembly view of a reducer mechanism of the present invention.
Figure 3:
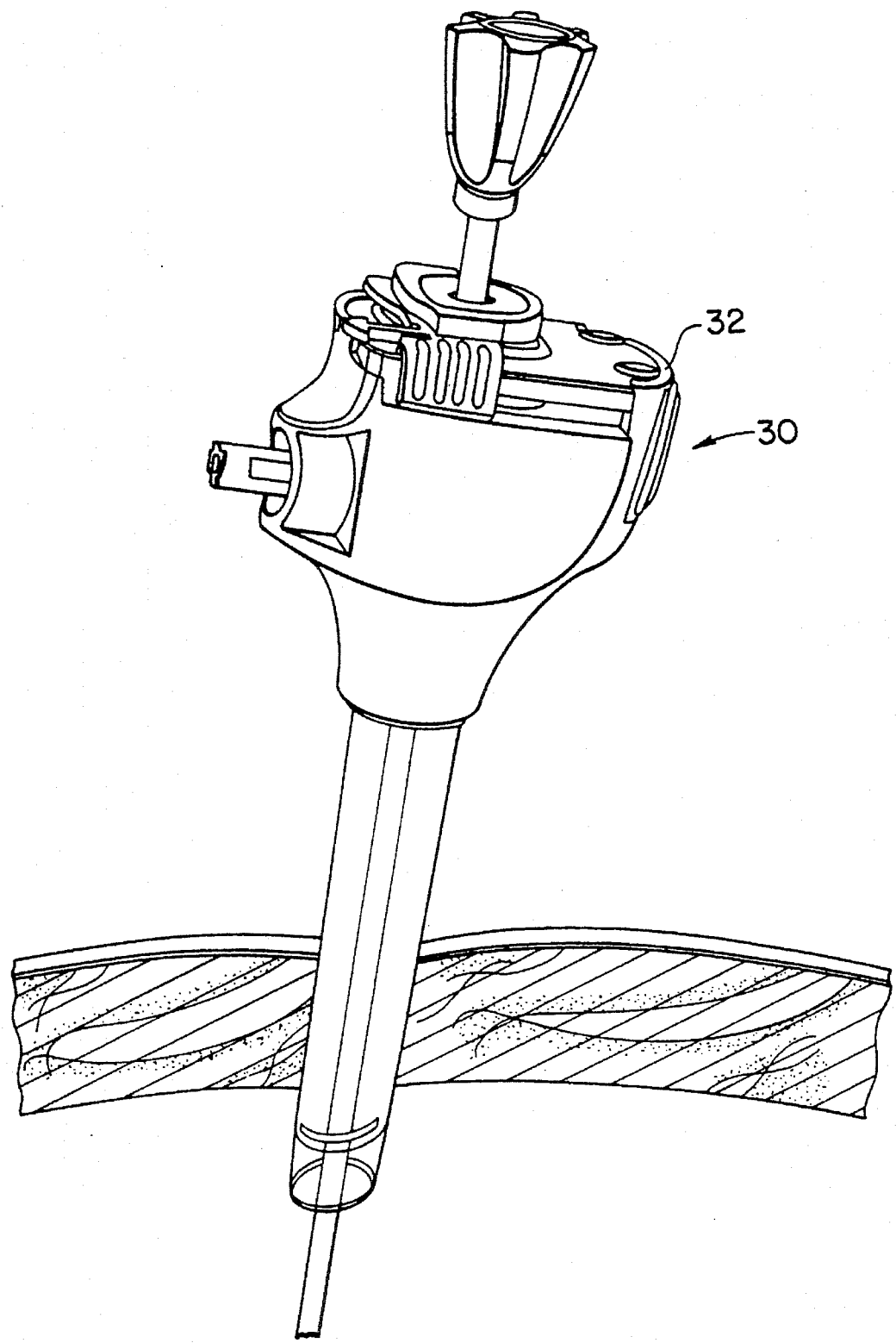
FIG. 3 is a perspective view of operation of the trocar seal of the present invention.

The reducer sealing device 100 of the present invention can be best seen in FIGS. 2–4. It consists of a reducer track 110 which fits within the lip 32 of the cannula handle 30. This reducer track 110 contains an opening 112 generally the same size as the opening R of the cannula. Matable with this reducer track 110 is a reducer seal 120 and a reducer seal retainer 130. The reducer seal retainer 130 contains a number of posts 132, generally four, which mate with holes 122 on the reducer seal 120. The reducer seal 120 and reducer seal retainer 130 fit within the underside 142 of a reducer slide 140. The reducer slide 140 and reducer seal retainer 130 therefore form one integral unit. The reducer seal retainer 130 and reducer slide 140 have an opening O and reducer seal 120 an opening O' all of a smaller dimension than the dimension of the opening 112 of the reducer track 110. Thus, a smaller laparoscopic instrument is intended to be used with the reducer slide 140 in place over the reducer track 110.

The reducer track 110 contains a part of slide mechanisms 114 which frictionally engage the rails 144 on the reducer slide 140. Thus, the peripheral rib 120a of the reducer seal 120 is frictionally engaged with the reducer track 110 in a position to allow insertion of a relatively larger diameter laparoscopic instrument. This frictional engagement of the reducer seal and reducer track prevents the escape of gas. Thereafter, if desired the user pushes the reducer retainer and reducer slide 130/140 over the reducer track opening 112. This is done by moving the reducer slide 140 over the opening 112 so that the rails 144 on the reducer slide move over the slides 114 contained on the reducer track which mate with them. Thereafter, the reducer slide 140 presents a smaller diameter opening to the cannula handle 30. In this position, a lock on the reducer slide 140 engages a mating lock contained either on the reducer track 110 (not shown) or on the cannula handle 30. Of course, it is desirable to place this lock on the cannula handle 30, in that this helps create a more stable mechanism.

An alternate embodiment of the present invention incorporates aspects of the first embodiment with the use of a flip cap combination so that a third, still smaller diameter opening O can be used with the reducer mechanism. As seen in FIGS. 5–7, a reducer 200 contains a opening O of a 18–33 millimeters, but generally, less than the opening R in the cannula. This plate 200 fits capably onto the cannula handle 30. The plate itself contains a slide mechanism similar to the reducer slide shown in FIGS. 2–5. There is contained an opening R' in this slide mechanism of roughly 1–10 mm. In this aspect, the invention operates quite similarly to the embodiment shown in FIGS. 2–4. However, in addition to the reducer slide there is also contained a flip top cap 250 which contains yet another intermediate diameter O" (10–18 mm) than the opening in the reducer slide 100. Consequently, if it is desired to present an even smaller diameter for use with this cannula, the user maintains the slide in position over the cannula 20, and flips the reducer cap 250 over the reducer slide 100. Thus, the reducer cap 250 pivots around pivot points 260 contained the plate 210 of the mechanism 200. Thereafter, the cap 250 is aligned with the opening O in the plate 200. In this way, a generally even smaller dimension is presented to the user, usually on the order of 1 to 3 mm. Thus, a variety of openings may be presentable to the user with the reducer cap of the present invention. In this way, the user at his or her option, is able to present a number of different sized openings for use, and therefore derive greater flexibility of a trocar cannula.

It will be readily understood that the present invention is to be described by the attached claims and their equivalents.

What is claimed is:

1. In combination:
   a trocar cannula having a cylindrical opening with an inner diameter, and a cannula handle attached to said cannula, said cannula handle having a cylindrical opening extending therethrough; and
   said handle having a proximal end containing a planar surface; and a lip on the perimeter of said surface, said lip having a height extending from said surface in a proximal direction; and said handle cylindrical opening extending through said planar surface; and
   a reducer mechanism attached to said planar surface and slidable with respect thereto, said reducer mechanism having an opening with a smaller inner diameter than said opening in said cannula handle, and said reducer mechanism having a height extending from said lip surface in a proximal dimension said reducer height no greater than the height of said lip; and
   wherein said reducer mechanism is removably attached to said handle.

2. The combination of claim 1 further containing a plurality of detents on said planar surface, wherein said reducer mechanism is able to be retained by said detents in a position wherein said handle opening and said reducer mechanism opening are not aligned.

3. The combination of claim 1 further containing a plurality of detents on said planar surface, wherein said reducer mechanism is able to be retained by said detents in a position wherein said handle opening and said reducer mechanism opening are aligned.

4. The combination of claim 1 wherein said cannula opening is between 1 mm–33 mm.

5. The combination of claim 1 wherein said reducer mechanism opening is between 1 mm–18 mm.

6. In combination:
   a trocar cannula having a cylindrical opening with an inner diameter, and a cannula handle attached to said cannula, said cannula handle having a cylindrical opening extending therethrough; and
   said handle having a proximal end containing a planar surface; and said handle cylindrical opening extending through said planar surface; and
   a reducer mechanism attached to said planar surface and slidable with respect thereto, said reducer mechanism having an opening with a smaller inner diameter than said opening in said cannula handle; and
   a flip top mechanism attached to said reducer, said flip top having a plate with a cylindrical opening thereon, said cylindrical opening of said plate different than that of said reducer mechanism plate opening and said cannula handle opening.

7. The combination of claim 6 wherein said handle has a lip having a height extending from said planar surface in a proximal direction, and said reducer mechanism having a proximal direction less than said lip height.

8. The combination of claim 6 further containing a plurality of detents on said planar surface, wherein said reducer mechanism is able to be retained by said detents in a position wherein said handle opening and said reducer mechanism opening are not aligned.

9. The combination of claim 6 further containing a plurality of detents on said planar surface, wherein said reducer mechanism is able to be retained by said detents in a position wherein said handle opening and said reducer mechanism opening are aligned.

10. The combination of claim 6 wherein said cannula opening is between 1 mm–33 mm.

11. The combination of claim 6 wherein said reducer mechanism opening is between 1 mm–18 mm.

12. The combination of claim 6 wherein said flip top opening is between 1 mm–18 mm.

13. The combination of claim 6 wherein said flip top is capable of being latched to one of said reducer mechanism or said cannula handle.

14. The combination of claim 6 where reducer mechanism is removably attached to said handle.

* * * * *